(12) United States Patent
Czarnik

(10) Patent No.: US 7,842,675 B2
(45) Date of Patent: Nov. 30, 2010

(54) DEUTERIUM-ENRICHED CAPECITABINE

(75) Inventor: Anthony W. Czarnik, Reno, NV (US)

(73) Assignee: Protia, LLC, Reno, NV (US)

( * ) Notice: Subject to any disclaimer, the term of this patent is extended or adjusted under 35 U.S.C. 154(b) by 321 days.

(21) Appl. No.: 12/196,236

(22) Filed: Aug. 21, 2008

(65) Prior Publication Data

US 2009/0075931 A1 Mar. 19, 2009

Related U.S. Application Data

(60) Provisional application No. 60/972,764, filed on Sep. 15, 2007.

(51) Int. Cl.
*A01N 43/04* (2006.01)
*A61K 31/70* (2006.01)
(52) U.S. Cl. .......................................... 514/49; 514/43
(58) Field of Classification Search ....................... None
See application file for complete search history.

(56) References Cited

U.S. PATENT DOCUMENTS 5,472,949 A 12/1995 Arasaki et al.

FOREIGN PATENT DOCUMENTS

WO 26325 A2 10/1995

OTHER PUBLICATIONS

Schuller et al. Cancer Chemother. Pharmacol. (2000), vol. 45, pp. 291-297.*
Kushner, D.J.; Pharmacological Uses and Perspectives of Heavy Water and Deuterated Compounds; Canadian Journal of Physiology and Pharmacology 1999, 77(2), 79-88.

* cited by examiner

*Primary Examiner*—Patrick T Lewis
(74) *Attorney, Agent, or Firm*—Vance Intellectual Property, PC

(57) ABSTRACT

The present application describes deuterium-enriched capecitabine, pharmaceutically acceptable salt forms thereof, and methods of treating using the same.

20 Claims, No Drawings

DEUTERIUM-ENRICHED CAPECITABINE

CROSS-REFERENCE TO RELATED APPLICATIONS

The present application claims priority benefit under 35 U.S.C. §119(e) of U.S. Provisional Patent Application Ser. No. 60/972,764 filed 15 Sep. 2007. The disclosure of this application is incorporated herein by reference.

FIELD OF THE INVENTION

This invention relates generally to deuterium-enriched capecitabine, pharmaceutical compositions containing the same, and methods of using the same.

BACKGROUND OF THE INVENTION

Capecitabine, shown below, is a well known fluoropyrimidine carbamate with antineoplastic activity.

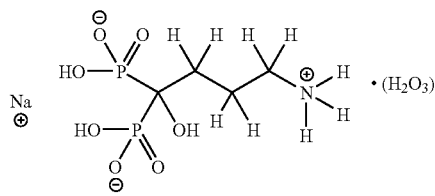

Since capecitabine is a known and useful pharmaceutical, it is desirable to discover novel derivatives thereof. Capecitabine is described in U.S. Pat. No. 5,472,949; the contents of which are incorporated herein by reference.

SUMMARY OF THE INVENTION

Accordingly, one object of the present invention is to provide deuterium-enriched capecitabine or a pharmaceutically acceptable salt thereof.

It is another object of the present invention to provide pharmaceutical compositions comprising a pharmaceutically acceptable carrier and a therapeutically effective amount of at least one of the deuterium-enriched compounds of the present invention or a pharmaceutically acceptable salt thereof.

It is another object of the present invention to provide a method for treating metastatic breast cancer, comprising administering to a host in need of such treatment a therapeutically effective amount of at least one of the deuterium-enriched compounds of the present invention or a pharmaceutically acceptable salt thereof.

It is another object of the present invention to provide a novel deuterium-enriched capecitabine or a pharmaceutically acceptable salt thereof for use in therapy.

It is another object of the present invention to provide the use of a novel deuterium-enriched capecitabine or a pharmaceutically acceptable salt thereof for the manufacture of a medicament (e.g., for the treatment of metastatic breast cancer).

These and other objects, which will become apparent during the following detailed description, have been achieved by the inventor's discovery of the presently claimed deuterium-enriched capecitabine.

DETAILED DESCRIPTION OF PREFERRED EMBODIMENTS

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

The present invention provides deuterium-enriched capecitabine or a pharmaceutically acceptable salt thereof. There are twenty-two hydrogen atoms in the capecitabine portion of capecitabine as show by variables $R_1$-$R_{22}$ in formula I below.

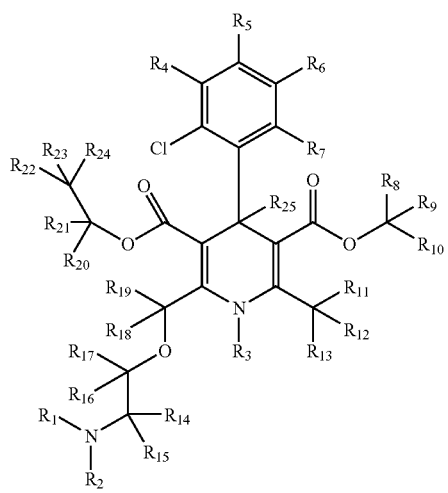

The hydrogens present on capecitabine have different capacities for exchange with deuterium. Hydrogen atoms $R_1$-$R_3$ are easily exchangeable under physiological conditions and, if replaced by deuterium atoms, it is expected that they will readily exchange for protons after administration to a patient. The remaining hydrogen atoms are not easily exchangeable for deuterium atoms. However, deuterium atoms at the remaining positions may be incorporated by the use of deuterated starting materials or intermediates during the construction of capecitabine.

The present invention is based on increasing the amount of deuterium present in capecitabine above its natural abundance. This increasing is called enrichment or deuterium-enrichment. If not specifically noted, the percentage of enrichment refers to the percentage of deuterium present in the compound, mixture of compounds, or composition. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Since there are 22 hydrogens in capecitabine, replacement of a single hydrogen atom with deuterium would result in a molecule with about 5% deuterium enrichment. In order to achieve enrichment less than about 5%, but above the natural abundance, only partial deuteration of one site is required. Thus, less than about 5% enrichment would still refer to deuterium-enriched capecitabine.

With the natural abundance of deuterium being 0.015%, one would expect that for approximately every 6,667 molecules of capecitabine (1/0.00015=6,667), there is one naturally occurring molecule with one deuterium present. Since capecitabine has 22 positions, one would roughly expect that for approximately every 146,674 molecules of capecitabine (22×6,667), all 22 different, naturally occurring, mono-deuterated capecitabines would be present. This approximation is a rough estimate as it doesn't take into account the different exchange rates of the hydrogen atoms on capecitabine. For naturally occurring molecules with more than one deuterium, the numbers become vastly larger. In view of this natural abundance, the present invention, in an embodiment, relates to an amount of an deuterium enriched compound, whereby the enrichment recited will be more than naturally occurring deuterated molecules.

In view of the natural abundance of deuterium-enriched capecitabine, the present invention also relates to isolated or purified deuterium-enriched capecitabine. The isolated or purified deuterium-enriched capecitabine is a group of molecules whose deuterium levels are above the naturally occurring levels (e.g., 5%). The isolated or purified deuterium-enriched capecitabine can be obtained by techniques known to those of skill in the art (e.g., see the syntheses described below).

The present invention also relates to compositions comprising deuterium-enriched capecitabine. The compositions require the presence of deuterium-enriched capecitabine which is greater than its natural abundance. For example, the compositions of the present invention can comprise (a) a μg of a deuterium-enriched capecitabine; (b) a mg of a deuterium-enriched capecitabine; and, (c) a gram of a deuterium-enriched capecitabine.

In an embodiment, the present invention provides an amount of a novel deuterium-enriched capecitabine.

Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another embodiment, the present invention provides a novel, deuterium enriched compound of formula I or a pharmaceutically acceptable salt thereof.

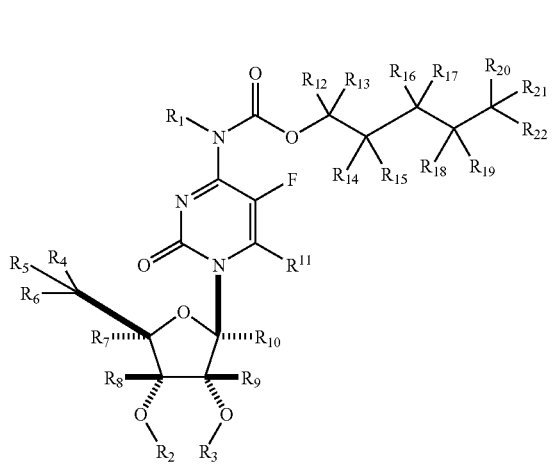

wherein $R_1$-$R_{22}$ are independently selected from H and D; and the abundance of deuterium in $R_1$-$R_{22}$ is at least 5%. The abundance can also be (a) at least 8%, (b) at least 12%, (c) at least 16%, (d) at least 20%, (e) at least 25%, (f) at least 28%, (g) at least 32%, (h) at least 36%, (i) at least 40%, (j) at least 45%, (k) at least 48%, (l) at least 52%, (m) at least 56%, (n) at least 60%, (o) at least 65%, (p) at least 68%, (q) at least 72%, (r) at least 76%, (s) at least 80%, (t) at least 85%, (u) at least 88%, (v) at least 92%, (w) at least 96%, and (y) 100%.

In another embodiment, the present invention provides a novel, deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides a novel, deuterium enriched compound of formula I or a pharmaceutically acceptable salt thereof, wherein the abundance of deuterium in $R_4$-$R_6$ is at least 33%. The abundance can also be (a) at least 67%, and (b) 100%.

In another embodiment, the present invention provides a novel, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides a novel, deuterium enriched compound of formula I, wherein the abundance of deuterium in $R_{11}$ is 100%.

In another embodiment, the present invention provides a novel, deuterium enriched compound of formula I or a pharmaceutically acceptable salt thereof, wherein the abundance of deuterium in $R_{12}$-$R_2$, is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides an isolated novel, deuterium enriched compound of formula I or a pharmaceutically acceptable salt thereof.

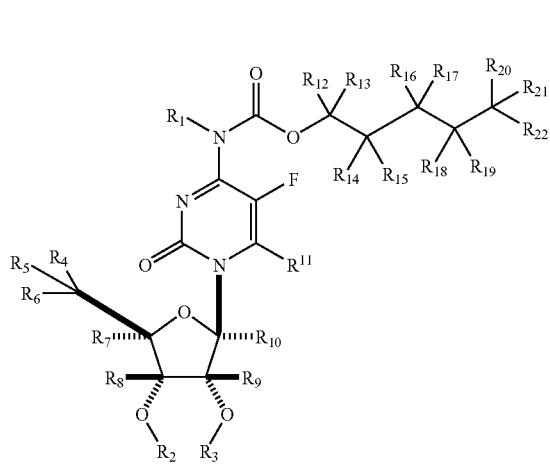

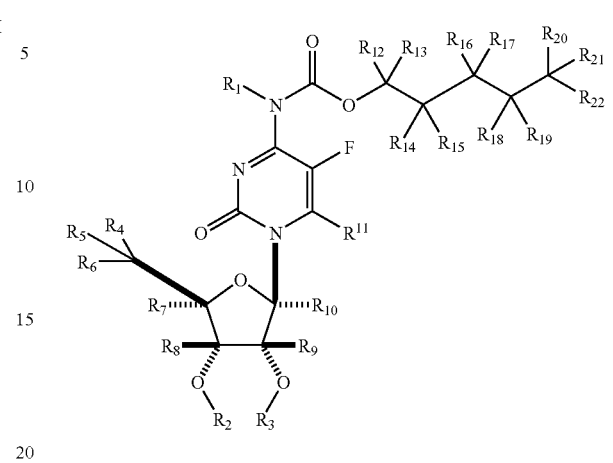

wherein $R_1$-$R_{22}$ are independently selected from H and D; and the abundance of deuterium in $R_1$-$R_{22}$ is at least 5%. The abundance can also be (a) at least 8%, (b) at least 12%, (c) at least 16%, (d) at least 20%, (e) at least 25%, (f) at least 28%, (g) at least 32%, (h) at least 36%, (i) at least 40%, (j) at least 45%, (k) at least 48%, (l) at least 52%, (m) at least 56%, (n) at least 60%, (o) at least 65%, (p) at least 68%, (q) at least 72%, (r) at least 76%, (s) at least 80%, (t) at least 85%, (u) at least 88%, (v) at least 92%, (w) at least 96%, and (y) 100%.

In another embodiment, the present invention provides an isolated novel, deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides an isolated novel, deuterium enriched compound of formula I or a pharmaceutically acceptable salt thereof, wherein the abundance of deuterium in $R_4$-$R_6$ is at least 33%. The abundance can also be (a) at least 67%, and (b) 100%.

In another embodiment, the present invention provides an isolated novel, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides an isolated novel, deuterium enriched compound of formula I, wherein the abundance of deuterium in $R_{11}$ is 100%.

In another embodiment, the present invention provides an isolated novel, deuterium enriched compound of formula I or a pharmaceutically acceptable salt thereof, wherein the abundance of deuterium in $R_{12}$-$R_{21}$ is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides novel mixture of deuterium enriched compounds of formula I or a pharmaceutically acceptable salt thereof.

wherein $R_1$-$R_{22}$ are independently selected from H and D; and the abundance of deuterium in $R_1$-$R_{22}$ is at least 5%. The abundance can also be (a) at least 8%, (b) at least 12%, (c) at least 16%, (d) at least 20%, (e) at least 25%, (f) at least 28%, (g) at least 32%, (h) at least 36%, (i) at least 40%, (j) at least 45%, (k) at least 48%, (l) at least 52%, (m) at least 56%, (n) at least 60%, (o) at least 65%, (p) at least 68%, (q) at least 72%, (r) at least 76%, (s) at least 80%, (t) at least 85%, (u) at least 88%, (v) at least 92%, (w) at least 96%, and (y) 100%.

In another embodiment, the present invention provides a novel mixture of, deuterium enriched compound of formula I or a pharmaceutically acceptable salt thereof, wherein the abundance of deuterium in $R_1$-$R_3$ is at least 33%. The abundance can also be (a) at least 67%, and (b) 100%.

In another embodiment, the present invention provides a novel mixture of, deuterium enriched compound of formula I or a pharmaceutically acceptable salt thereof, wherein the abundance of deuterium in $R_4$-$R_6$ is at least 33%. The abundance can also be (a) at least 67%, and (b) 100%.

In another embodiment, the present invention provides a novel mixture of, deuterium enriched compound of formula I or a pharmaceutically acceptable salt thereof, wherein the abundance of deuterium in $R_7$-$R_{10}$ is at least 25%. The abundance can also be (a) at least 50%, (b) at least 75%, and (c) 100%.

In another embodiment, the present invention provides a novel mixture of, deuterium enriched compound of formula I, wherein the abundance of deuterium in $R_{11}$ is 100%.

In another embodiment, the present invention provides a novel mixture of, deuterium enriched compound of formula I or a pharmaceutically acceptable salt thereof, wherein the abundance of deuterium in $R_{12}$-$R_{21}$ is at least 10%. The abundance can also be (a) at least 20%, (b) at least 30%, (c) at least 40%, (d) at least 50%, (e) at least 60%, (f) at least 70%, (g) at least 80%, (h) at least 90%, and (i) 100%.

In another embodiment, the present invention provides novel pharmaceutical compositions, comprising: a pharmaceutically acceptable carrier and a therapeutically effective amount of a deuterium-enriched compound of the present invention.

In another embodiment, the present invention provides a novel method for treating metastatic breast cancer comprising: administering to a patient in need thereof a therapeutically effective amount of a deuterium-enriched compound of the present invention.

In another embodiment, the present invention provides an amount of a deuterium-enriched compound of the present invention as described above for use in therapy.

In another embodiment, the present invention provides the use of an amount of a deuterium-enriched compound of the present invention for the manufacture of a medicament (e.g., for the treatment of metastatic breast cancer).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to the recited examples.

The compounds of the present invention may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present invention.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the present invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

EXAMPLES

Table 1 provides compounds that are representative examples of the present invention. When one of $R_1$-$R_{22}$ is present, it is selected from H or D.

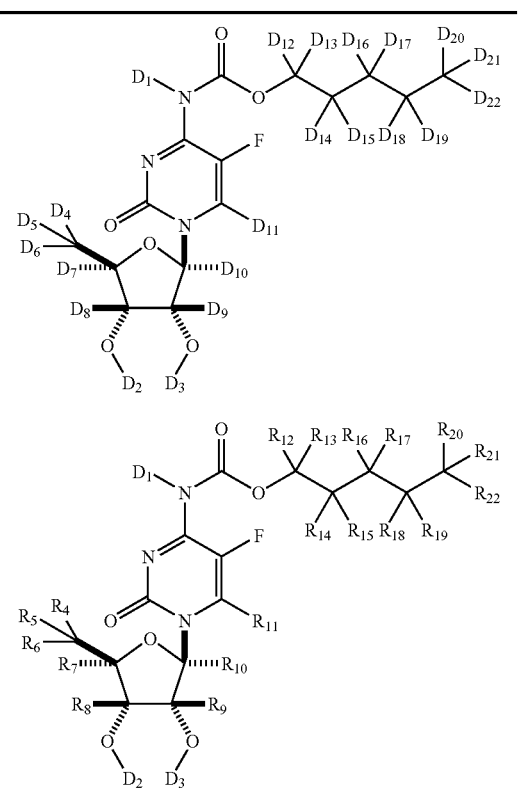

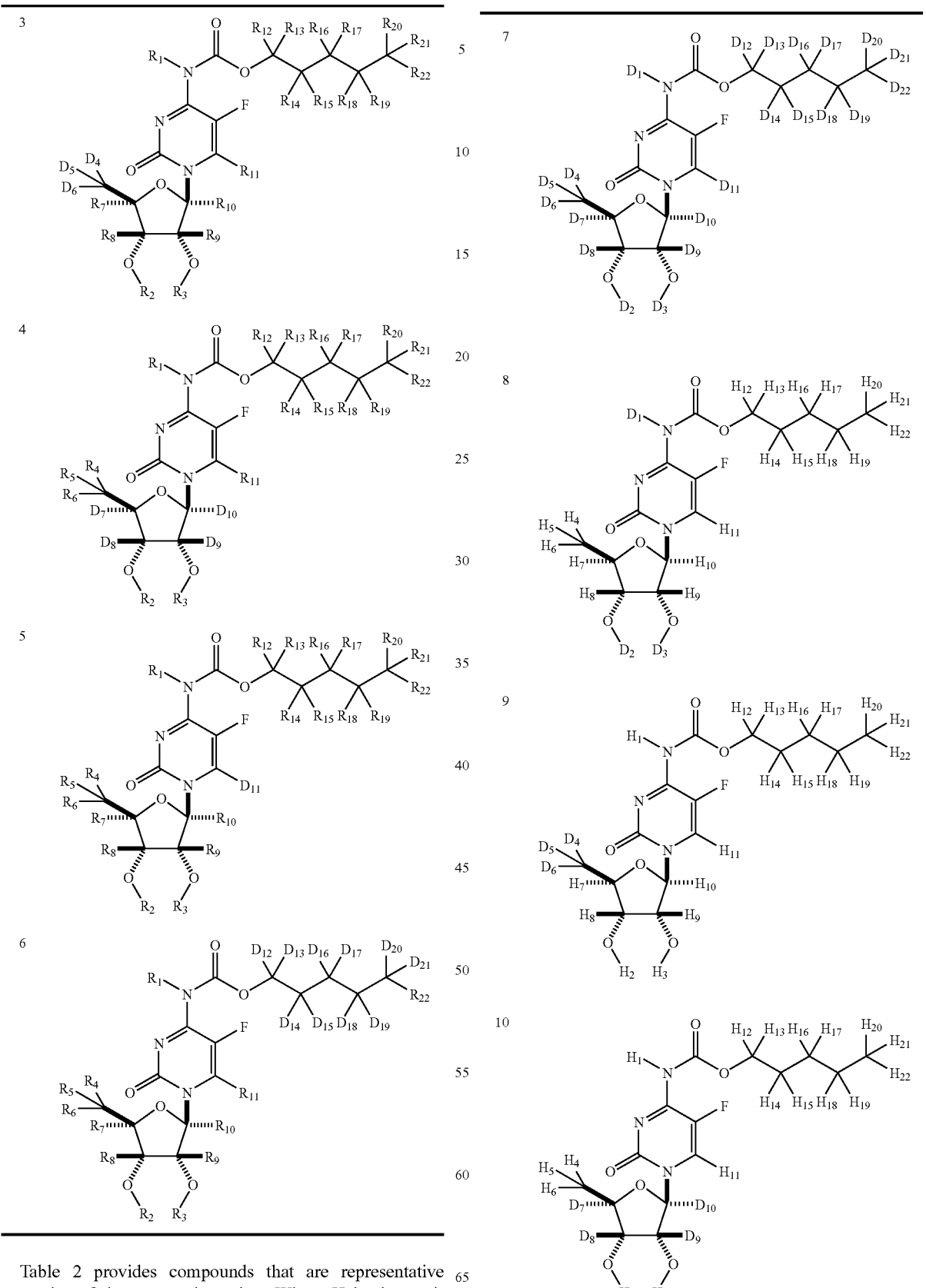
Table 2 provides compounds that are representative examples of the present invention. Where H is shown, it represents naturally abundant hydrogen.

-continued

11

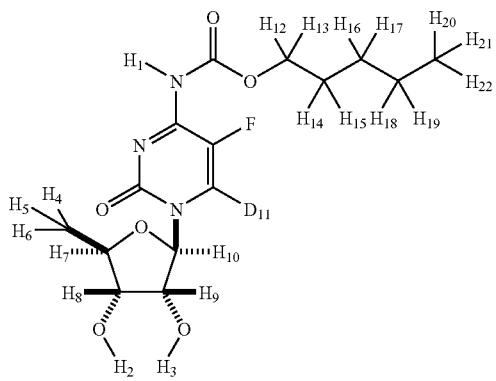

12

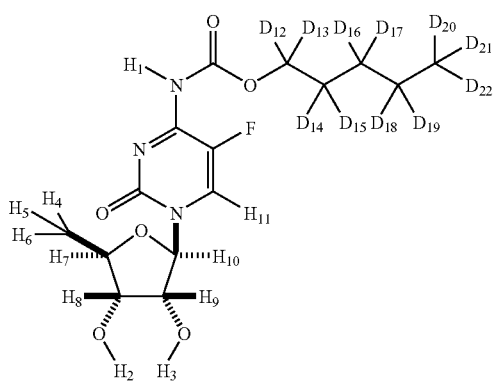

Numerous modifications and variations of the present invention are possible in light of the above teachings. It is therefore to be understood that within the scope of the appended claims, the invention may be practiced otherwise that as specifically described herein.

What is claimed is:

1. A deuterium-enriched compound of formula I or a pharmaceutically acceptable salt thereof:

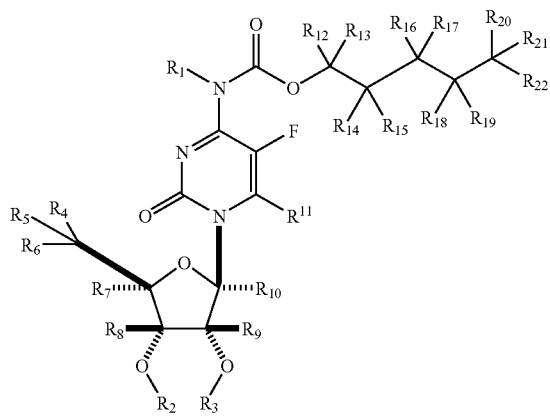

wherein $R_1$-$R_{22}$ are independently selected from H and D; and the abundance of deuterium in $R_1$-$R_{22}$ is at least 5%.

2. A deuterium-enriched compound of claim 1, wherein the abundance of deuterium in $R_1$-$R_{22}$ is selected from at least 5%, at least 9%, at least 14%, at least 18%, at least 23%, at least 27%, at least 32%, at least 36%, at least 41%, at least 45%, at least 50%, at least 55%, at least 59%, at least 64%, at least 68%, at least 73%, at least 77%, at least 82%, at least 86%, at least 91%, at least 95%, and 100%.

3. A deuterium-enriched compound of claim 1, wherein the abundance of deuterium in $R_1$-$R_3$ is selected from at least 33%, at least 67%, and 100%.

4. A deuterium-enriched compound of claim 1, wherein the abundance of deuterium in $R_4$-$R_6$ is selected from at least 33%, at least 67%, and 100%.

5. A deuterium-enriched compound of claim 1, wherein the abundance of deuterium in $R_7$-$R_{10}$ is selected from at least 25%, at least 50%, at least 75%, and 100%.

6. A deuterium-enriched compound of claim 1, wherein the abundance of deuterium in $R_{11}$ is 100%.

7. A deuterium-enriched compound of claim 1, wherein the abundance of deuterium in $R_{12}$-$R_{21}$ is selected from at least 10%, at least 20%, at least 30%, at least 40%, at least 50%, at least 60%, at least 70%, at least 80%, at least 90%, and 100%.

8. A deuterium-enriched compound of claim 1, wherein the compound is selected from compounds 1-6 of Table 1.

9. A deuterium-enriched compound of claim 1, wherein the compound is selected from compounds 7-12 of Table 2.

10. An isolated deuterium-enriched compound of formula I or a pharmaceutically acceptable salt thereof:

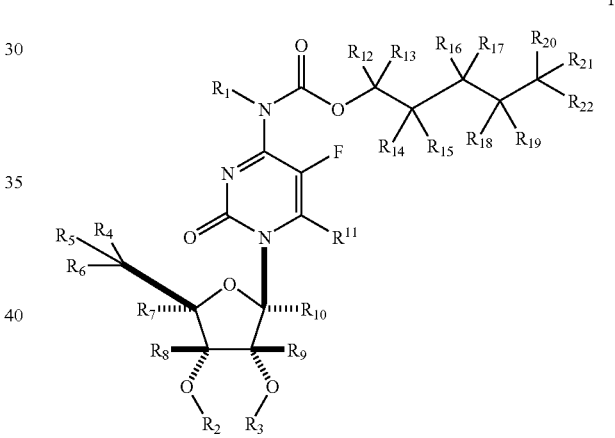

wherein $R_1$-$R_{22}$ are independently selected from H and D; and the abundance of deuterium in $R_1$-$R_{22}$ is at least 5%.

11. An isolated deuterium-enriched compound of claim 10, wherein the abundance of deuterium in $R_1$-$R_{22}$ is selected from at least 5%, at least 9%, at least 14%, at least 18%, at least 23%, at least 27%, at least 32%, at least 36%, at least 41%, at least 45%, at least 50%, at least 55%, at least 59%, at least 64%, at least 68%, at least 73%, at least 77%, at least 82%, at least 86%, at least 91%, at least 95%, and 100%.

12. An isolated deuterium-enriched compound of claim 10, wherein the abundance of deuterium in $R_1$-$R_3$ is selected from at least 33%, at least 67%, and 100%.

13. An isolated deuterium-enriched compound of claim 10, wherein the abundance of deuterium in $R_4$-$R_6$ is selected from at least 33%, at least 67%, and 100%.

14. An isolated deuterium-enriched compound of claim 10, wherein the compound is selected from compounds 1-6 of Table 1.

15. An isolated deuterium-enriched compound of claim 10, wherein the compound is selected from compounds 7-12 of Table 2.

16. A mixture of deuterium-enriched compounds of formula I or a pharmaceutically acceptable salt thereof:

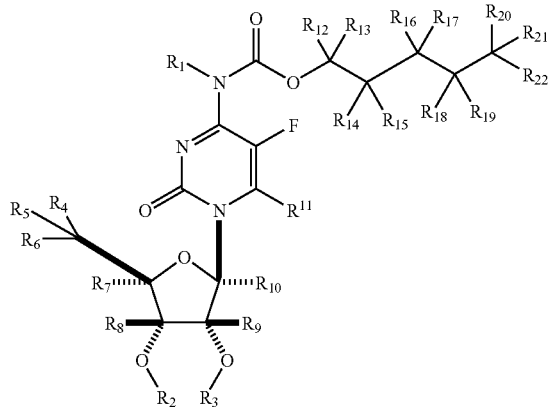

wherein $R_1$-$R_{22}$ are independently selected from H and D; and the abundance of deuterium in $R_1$-$R_{22}$ is at least 5%.

17. A mixture of deuterium-enriched compound of claim 16, wherein the compound is selected from compounds 1-6 of Table 1.

18. A mixture of deuterium-enriched compound of claim 16, wherein the compound is selected from compounds 7-12 of Table 2.

19. A pharmaceutical composition, comprising: a pharmaceutically acceptable carrier and a therapeutically effective amount of a compound of claim 1 or a pharmaceutically acceptable salt form thereof.

20. A method for treating metastatic breast cancer comprising: administering, to a patient in need thereof, a therapeutically effective amount of a compound of claim 1 or a pharmaceutically acceptable salt form thereof.

* * * * *